(12) United States Patent
Prescott et al.

(10) Patent No.: US 10,548,598 B2
(45) Date of Patent: *Feb. 4, 2020

(54) CIRCULAR SURGICAL STAPLING DEVICE INCLUDING BUTTRESS MATERIAL

(71) Applicant: Covidien LP, Mansfield, MA (US)

(72) Inventors: Michael Prescott, Hamden, CT (US); Richard P. Stevenson, Colchester, CT (US)

(73) Assignee: COVIDIEN LP, Mansfield, MA (US)

( * ) Notice: Subject to any disclaimer, the term of this patent is extended or adjusted under 35 U.S.C. 154(b) by 291 days.

This patent is subject to a terminal disclaimer.

(21) Appl. No.: 15/590,332

(22) Filed: May 9, 2017

(65) Prior Publication Data

US 2017/0238931 A1    Aug. 24, 2017

Related U.S. Application Data

(63) Continuation of application No. 14/064,280, filed on Oct. 28, 2013, now Pat. No. 9,655,620.

(51) Int. Cl.
*A61B 17/072* (2006.01)
*A61B 17/115* (2006.01)

(52) U.S. Cl.
CPC .... *A61B 17/07292* (2013.01); *A61B 17/1155* (2013.01); *A61B 2017/07257* (2013.01); *A61B 2017/07285* (2013.01)

(58) Field of Classification Search
CPC .............................. A61B 17/068; A61B 17/115
USPC .......................... 227/176.1, 180.1, 179.1, 19
See application file for complete search history.

(56) References Cited

U.S. PATENT DOCUMENTS

| 3,054,406 | A | 9/1962 | Usher |
| 3,079,606 | A | 3/1963 | Bobrov et al. |
| 3,124,136 | A | 3/1964 | Usher |
| 3,490,675 | A | 1/1970 | Green et al. |
| 3,499,591 | A | 3/1970 | Green |

(Continued)

FOREIGN PATENT DOCUMENTS

| CA | 2 667 434 A1 | 5/2008 |
| CN | 101310680 A | 11/2008 |

(Continued)

OTHER PUBLICATIONS

Australian Examination Report No. 1 corresponding to counterpart Int'l Appln. No. AU 2012244380 dated May 20, 2016.

(Continued)

*Primary Examiner* — Nathaniel C Chukwurah (57) ABSTRACT

A buttress material and mounting structure assembly is provided for use with a circular surgical stapling device. The assembly comprises a ring-like mounting structure sized to have an outer diameter that frictionally engages a radial inner surface of a staple cartridge assembly, wherein the mounting structure is disposed within the radial inner surface of the staple cartridge assembly; an annular buttress material overlaying a tissue facing surface of the staple cartridge assembly, the annular buttress material defining an outer radial terminal edge extending radially beyond a pair of annular arrays of staple receiving slots, and a radial inner terminal edge extending across the mounting structure; and at least one suture securing the buttress material to the mounting structure.

19 Claims, 7 Drawing Sheets

(56) References Cited

U.S. PATENT DOCUMENTS

| | | |
|---|---|---|
| 3,797,494 A | 3/1974 | Zaffaroni |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,871,135 A | 2/1999 | Williamson, IV et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,142,933 A | 11/2000 | Longo et al. |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,016,177 B2 | 9/2011 | Bettuchi et al. |

(56) References Cited

U.S. PATENT DOCUMENTS

| | | |
|---|---|---|
| 8,016,178 B2 | 9/2011 | Olson et al. |
| 8,025,199 B2 | 9/2011 | Whitman et al. |
| 8,028,883 B2 | 10/2011 | Stopek |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,408,440 B2 | 4/2013 | Olson et al. |
| 8,413,869 B2 | 4/2013 | Heinrich |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,364,229 B2 | 6/2016 | D'Agostino et al. |
| 9,364,234 B2 | 6/2016 | (Prommersberger) Stopek et al. |
| 9,629,626 B2 | 4/2017 | Soltz et al. |
| 9,655,620 B2 * | 5/2017 | Prescott ............ A61B 17/1155 |
| 9,693,772 B2 | 7/2017 | Ingmanson et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,931,116 B2 | 4/2018 | Racenet et al. |
| 10,022,125 B2 | 7/2018 | (Prommersberger) Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0028243 A1 | 3/2002 | Masters |
| 2002/0091397 A1 | 7/2002 | Chen |
| 2002/0151911 A1 | 10/2002 | Gabbay |
| 2002/0165563 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios et al. |
| 2003/0125676 A1 | 7/2003 | Swenson et al. |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |

(56) References Cited

U.S. PATENT DOCUMENTS

| | | |
|---|---|---|
| 2005/0283256 A1 | 12/2005 | Sommerich et al. |
| 2006/0004407 A1 | 1/2006 | Hiles et al. |
| 2006/0085030 A1 | 4/2006 | Bettuchi et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0190027 A1 | 8/2006 | Downey |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1* | 10/2007 | Pace-Floridia ............ A61B 17/07207 227/175.1 |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0031842 A1 | 2/2009 | Kawai et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1* | 5/2009 | Murray ............ A61B 17/00491 227/180.1 |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016855 A1 | 1/2010 | Ramstein et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0174253 A1 | 7/2010 | Cline et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331859 A1 | 12/2010 | Omori |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0034910 A1 | 2/2011 | Ross et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0174099 A1 | 7/2011 | Ross et al. |
| 2011/0215132 A1 | 9/2011 | Aranyi et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0187179 A1 | 7/2012 | Gleiman |
| 2012/0197272 A1 | 8/2012 | Oray et al. |
| 2012/0241491 A1 | 9/2012 | Aldridge et al. |
| 2012/0241499 A1 | 9/2012 | Baxter, III et al. |
| 2012/0253298 A1 | 10/2012 | Henderson et al. |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Olson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | (Prommersberger) Stopek et al. |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |

(56) References Cited

U.S. PATENT DOCUMENTS

| | | |
|---|---|---|
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0224686 A1 | 8/2014 | Aronhalt et al. |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0133995 A1 | 5/2015 | Shelton, IV et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0367253 A1 | 12/2016 | Hodgkinson |
| 2017/0119390 A1 | 5/2017 | Schellin et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | (Prommersberger) Stopek et al. |
| 2019/0021734 A1 | 1/2019 | Hodgkinson |
| 2019/0059878 A1 | 2/2019 | (Tarinelli) Racenet et al. |
| 2019/0083087 A1 | 3/2019 | Viola et al. |

FOREIGN PATENT DOCUMENTS

| | | |
|---|---|---|
| CN | 101332110 A | 12/2008 |
| DE | 1 99 24 311 A1 | 11/2000 |
| EP | 0327022 A2 | 8/1989 |
| EP | 0594148 A1 | 4/1994 |
| EP | 0667119 A1 | 8/1995 |
| EP | 1064883 A1 | 1/2001 |
| EP | 1256317 A2 | 11/2002 |
| EP | 1256318 A1 | 11/2002 |
| EP | 1520525 A1 | 4/2005 |
| EP | 1621141 A2 | 2/2006 |
| EP | 1702570 A1 | 9/2006 |
| EP | 1759640 A2 | 3/2007 |
| EP | 1815804 A2 | 8/2007 |
| EP | 1825820 A1 | 8/2007 |
| EP | 1929958 A2 | 6/2008 |
| EP | 1994890 A1 | 11/2008 |
| EP | 2005894 A2 | 12/2008 |
| EP | 2005895 A2 | 12/2008 |
| EP | 2008595 A2 | 12/2008 |
| EP | 2039308 A2 | 3/2009 |
| EP | 2090231 A1 | 8/2009 |
| EP | 2090244 A2 | 8/2009 |
| EP | 2090252 A2 | 8/2009 |
| EP | 2163211 A2 | 3/2010 |
| EP | 2189121 A1 | 5/2010 |
| EP | 2198787 A1 | 6/2010 |
| EP | 2236098 A2 | 10/2010 |
| EP | 2236099 A1 | 10/2010 |
| EP | 2258282 A2 | 12/2010 |
| EP | 2292276 A2 | 3/2011 |
| EP | 2311386 A2 | 4/2011 |
| EP | 2436348 A1 | 4/2012 |
| EP | 2462880 A2 | 6/2012 |
| EP | 2491867 A1 | 8/2012 |
| EP | 2497431 A1 | 9/2012 |
| EP | 2517637 A1 | 10/2012 |
| EP | 2586380 A1 | 5/2013 |
| EP | 2604195 A1 | 6/2013 |
| EP | 2604197 A2 | 6/2013 |
| EP | 2620105 A1 | 7/2013 |
| EP | 2620106 A2 | 7/2013 |
| EP | 2630922 A1 | 8/2013 |
| EP | 2644125 A2 | 10/2013 |
| EP | 2762091 A2 | 8/2014 |
| JP | 2000166933 A | 6/2000 |
| JP | 2002202213 A | 7/2002 |
| JP | 2007124166 A | 5/2007 |
| WO | 9005489 A1 | 5/1990 |
| WO | 9516221 A1 | 6/1995 |
| WO | 9622055 A1 | 7/1996 |
| WO | 9701989 A1 | 1/1997 |
| WO | 9713463 A1 | 4/1997 |
| WO | 9817180 A1 | 4/1998 |
| WO | 9838923 A1 | 9/1998 |
| WO | 9945849 A1 | 9/1999 |
| WO | 03082126 A1 | 10/2003 |
| WO | 03088845 A2 | 10/2003 |
| WO | 03094743 A1 | 11/2003 |
| WO | 03105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
Chinese Third Office Action corresponding to counterpart Patent Application CN 201410588811.8 dated Mar. 11, 2019.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.

(56) References Cited

OTHER PUBLICATIONS

Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
European Search Report corresponding to EP 14190419.3, completed Mar. 24, 2015 and dated Mar. 30, 2015; (6 pp).
European Search Report corresponding to EP 05 02 2585.3, completed Jan. 25, 2006 and dated Feb. 3, 2006; 4 pages.
European Search Report corresponding to EP 06 00 4598, completed Jun. 22, 2006; 2 pages.
European Search Report corresponding to EP 06 01 6962.0, completed Jan. 3, 2007 and dated Jan. 11, 2007; 10 pages.
International Search Report corresponding to International Application No. PCT/US2005/036740, completed Feb. 20, 2007 and dated Mar. 23, 2007; 8 pages.
International Search Report corresponding to International Application No. PCT/US2007/022713, completed Apr. 21, 2008 and dated May 15, 2008; 1 page.
International Search Report corresponding to International Application No. PCT/US2008/002981, completed Jun. 9, 2008 and dated Jun. 26, 2008; 2 pages.
European Search Report corresponding to EP 08 25 1779, completed Jul. 14, 2008 and dated Jul. 23, 2008; 5 pages.
European Search Report corresponding to EP 08 25 1989.3, completed Mar. 11, 2010 and dated Mar. 24, 2010; 6 pages.
European Search Report corresponding to EP 10 25 0639.1, completed Jun. 17, 2010 and dated Jun. 28, 2010; 7 pages.
European Search Report corresponding to EP 10 25 0715.9, completed Jun. 30, 2010 and dated Jul. 20, 2010; 3 pages.
European Search Report corresponding to EP 05 80 4382.9, completed Oct. 5, 2010 and dated Oct. 12, 2010; 3 pages.
European Search Report corresponding to EP 10 25 1437.9, completed Nov. 22, 2010 and dated Dec. 16, 2010; 3 pages.
European Search Report corresponding to EP 09 25 2897.5, completed Feb. 7, 2011 and dated Feb. 15, 2011; 3 pages.
European Search Report corresponding to EP 10 25 0642.5, completed Mar. 25, 2011 and dated Apr. 4, 2011; 4 pages.
European Search Report corresponding to EP 11 18 8309.6, completed Dec. 15, 2011 and dated Jan. 12, 2012; 3 pages.
European Search Report corresponding to EP 12 15 2229.6, completed Feb. 23, 2012 and dated Mar. 1, 2012; 4 pages.
European Search Report corresponding to EP 12 15 0511.9, completed Apr. 16, 2012 and dated Apr. 24, 2012; 7 pages.
European Search Report corresponding to EP 12 15 2541.4, completed Apr. 23, 2012 and dated May 3, 2012; 10 pages.
European Search Report corresponding to EP 12 16 5609.4, completed Jul. 5, 2012 and dated Jul. 13, 2012; 8 pages.
European Search Report corresponding to EP 12 15 8861.0, completed Jul. 17, 2012 and dated Jul. 24, 2012; 9 pages.
European Search Report corresponding to EP 12 16 5878.5, completed Jul. 24, 2012 and dated Aug. 6, 2012; 8 pages.
Extended European Search Report corresponding to EP 12 19 1035.0, completed Jan. 11, 2013 and dated Jan. 18, 2013; 7 pages.
Extended European Search Report corresponding to EP 12 18 6175.1, completed Jan. 15, 2013 and dated Jan. 23, 2013; 7 pages.
Extended European Search Report corresponding to EP 12 19 1114.3, completed Jan. 23, 2013 and dated Jan. 31, 2013; 10 pages.
Extended European Search Report corresponding to EP 12 19 2224.9, completed Mar. 14, 2013 and dated Mar. 26, 2013; 8 pages.
Extended European Search Report corresponding to EP 12 19 6904.2, completed Mar. 2013 and dated Jul. 26, 2013; 8 pages.
Extended European Search Report corresponding to EP 12 19 6911.7, completed Apr. 18, 2013 and dated Apr. 24, 2013; 8 pages.
Extended European Search Report corresponding to EP 07 00 5842.5, completed May 13, 2013 and dated May 29, 2013; 7 pages.
Extended European Search Report corresponding to EP 12 19 8776.2, completed May 16, 2013 and dated May 27, 2013; 8 pages.
Extended European Search Report corresponding to EP 12 19 8749.9, completed May 21, 2013 and dated May 31, 2013; 8 pages.
Extended European Search Report corresponding to EP 13 15 6297.7, completed Jun. 4, 2013 and dated Jun. 13, 20131; 7 pages.
Extended European Search Report corresponding to EP 13 17 3985.6, completed Aug. 19, 2013 and dated Aug. 28, 2013; 6 pages.
Extended European Search Report corresponding to EP 13 17 3986.4, completed Aug. 20, 2013 and dated Aug. 29, 2013; 7 pages.
Extended European Search Report corresponding to EP 13 17 7437.4, completed Sep. 11, 2013 and dated Sep. 19, 2013; (6 pp).
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Chinese First Office Action corresponding to counterpart Chinese Patent Appln. No. CN 201410588811.8 dated Dec. 5, 2017.
European Office Action corresponding to counterpart European Appln. No. EP 15 17 4146.9 dated May 15, 2017.
Japanese Office Action corresponding to counterpart Japanese Appln. No. JP 2013-154561 dated May 23, 2017.
European Office Action corresponding to counterpart European Appln. No. EP 12 19 4784.0 dated May 29, 2017.
Japanese Office Action corresponding to counterpart Japanese Appln. No. JP 2013-169083 dated May 31, 2017.
Australian Examination Report No. 1 corresponding to counterpart Australian Appln. No. AU 2013213767 dated Jun. 29, 2017.
Australian Examination Report No. 2 corresponding to counterpart Australian Appln. No. AU 2012261752 dated Jul. 7, 2017.
Australian Examination Report No. 1 corresponding to counterpart Australian Appln. No. AU 2013266989 dated Jul. 10, 2017.
Extended European Search Report corresponding to counterpart European Appln. No. EP 14 15 3609.4 dated Jul. 14, 2017.
Australian Examination Report No. 1 corresponding to counterpart Australian Appln. No. AU 2013234418 dated Jul. 14, 2017.
Extended European Search Report corresponding to counterpart European Appln. No. EP 14 15 3610.2 dated Jul. 17, 2017.
Australian Examination Report No. 1 corresponding to counterpart Australian Appln. No. AU 2014200109 dated Jul. 20, 2017.
Australian Examination Report No. 1 corresponding to counterpart Australian Appln. No. AU 2014200074 dated Jul. 20, 2017.
Japanese Office Action corresponding to counterpart Japanese Appln. No. JP 2013-250857 dated Aug. 17, 2017.
Japanese Office Action corresponding to counterpart Japanese Appln. No. JP 2013-229471 dated Aug. 17, 2017.
Australian Examination Report No. 1 corresponding to counterpart Australian Appln. No. AU 2014200793 dated Sep. 2, 2017.

(56) References Cited

OTHER PUBLICATIONS

Extended European Search Report corresponding to counterpart European Appln. No. EP 17 17 8528.0 dated Oct. 13, 2017.
Australian Examination Report No. 1 corresponding to counterpart Australian Appln. No. AU 2013234420 dated Oct. 24, 2017.
Japanese Office Action corresponding to counterpart Japanese Appln. No. JP 2013-175379 dated Oct. 20, 2017.
Japanese Office Action corresponding to counterpart Japanese Appln. No. JP 2013-147701 dated Oct. 27, 2017.
Extended European Search Report corresponding to counterpart European Appln. No. EP 17 17 5656.2 dated Nov. 7, 2017.
Japanese Office Action corresponding to counterpart Japanese Appln. No. JP 2014-009738 dated Nov. 14, 2017.
European Office Action corresponding to counterpart European Appln. No. EP 13 17 3986.4 dated Nov. 29, 2017.
Japanese Office Action corresponding to counterpart Japanese Appln. No. JP 2017-075975 dated Dec. 4, 2017.
European Office Action corresponding to counterpart European Appln. No. EP 13 19 7958.5 dated Dec. 11, 2017.
Chinese Second Office Action corresponding to counterpart Patent Application CN 201410588811.8 dated Aug. 27, 2018.
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Extended European Search Report corresponding to EP 08 72 6500.5, completed Feb. 20, 2014 and dated Mar. 3, 2014; (7 pp).
Extended European Search Report corresponding to EP 13 19 5919.9, completed Feb. 10, 2014 and dated Mar. 3, 2014; (7 pp).
Extended European Search Report corresponding to EP 13 19 2123.1, completed Jan. 30, 2014 and dated Feb. 10, 2014; (8 pp).
Extended European Search Report corresponding to EP 13 19 6816.6, completed Mar. 28, 2014 and dated Apr. 9, 2014; (9 pp).
Extended European Search Report corresponding to EP 13 19 4995.0, completed Jun. 5, 2014 and dated Jun. 16, 2014; (5 pp).
Extended European Search Report corresponding to EP 13 19 5019.8, completed Mar. 14, 2014 and dated Mar. 24, 2014; (7 pp).
Extended European Search Report corresponding to EP 13 19 2111.6, completed Feb. 13, 2014 and dated Feb. 27, 2014; (10 pp).
Extended European Search Report corresponding to EP 13 19 7958.5, completed Apr. 4, 2014 and dated Apr. 15, 2014; (8 pp).
Extended European Search Report corresponding to EP 14 15 6342.9, completed Jul. 22, 2014 and dated Jul. 29, 2014; (8 pp).
Extended European Search Report corresponding to EP 14 15 7195.0, completed Jun. 5, 2014 and dated Jun. 18, 2014; (9 pp).
Chinese Notification of Reexamination corresponding to counterpart Int'l Appln. No. CN 201010517292.8 dated Jun. 2, 2015.
Japanese Office Action corresponding to counterpart Int'l Appln. No. JP 2014-216989 dated Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 dated Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.

* cited by examiner

CIRCULAR SURGICAL STAPLING DEVICE INCLUDING BUTTRESS MATERIAL

CROSS-REFERENCE TO RELATED APPLICATION

The present application is a Continuation Application which claims that benefit of and priority to U.S. patent application Ser. No. 14/064,280, filed on Oct. 28, 2013 (now U.S. Pat. No. 9,655,620), the entire content of which is incorporated herein by reference.

BACKGROUND

Technical Field

The present disclosure relates to surgical stapling devices and buttress materials for use with said surgical stapling device and, more particularly, to structures and methods for attaching a buttress material to a surgical stapling device for use in anastomosis procedures.

Background of Related Art

Staples have traditionally been used to replace suturing when joining or anastomosing various body structures such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of anastomoses. Linear surgical stapling devices generally include a pair of jaws or finger-like structures between which body tissue to be joined is placed. When the surgical stapling device is actuated and/or "fired", firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such surgical stapling devices are described in U.S. Pat. Nos. 4,354,628, 5,014,899 and 5,040,715, the entirety of each of which is incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples. Examples of such annular surgical stapling devices are described in U.S. Pat. Nos. 5,799,857 and 5,915,616 to Robertson et al., the entirety of each of which is incorporated herein by reference.

In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

For most procedures, the use of bare staples, with the staples in direct contact with the patient's tissue, is generally acceptable. The integrity of the tissue will normally serve to prevent the staples from tearing out of the tissue and compromising the sealing before healing has occurred. However, in some surgical operations, surgical supports, e.g., meshes or buttress materials, are employed by surgeons in combination with linear stapling devices to bridge, repair and/or reinforce tissue defects within a patient, especially those occurring in the abdominal wall, chest wall, diaphragm, and other musculo-aponeurotic areas of the body. Examples of suitable surgical supports are disclosed in U.S. Pat. Nos. 3,054,406, 3,124,136, 4,347,847, 4,655,221, 4,838,884, 5,002,551, and 7,942,890, the entirety of each of which is incorporated herein by reference.

When the staples are applied in surgical procedures utilizing surgical supports (i.e., reinforcing material), the legs of the staple typically pass from the cartridge jaw through a layer of the surgical support, and through the patient's tissue before encountering the anvil jaw.

While the surgical supports described above are used in conjunction with linear surgical stapling devices, the need exists for annular support structures for use in conjunction with annular or circular surgical stapling devices, for example, an end-to-end anastomosis stapler such as a Model "EEA™" instrument available from COVIDIEN LP, New Haven, Conn. and disclosed in U.S. Pat. No. 5,392,979 to Green et al.

One possible side effect of any end-to-end bowel anastomosis is its tendency to undergo stenosis over time, which can decrease the diameter of the lumen over time. Accordingly, the need exists for an annular surgical structure which operates in conjunction with any end-to-end, annular, or circular anastomosis or stapling device and assists in keeping open the lumen of the anastomosed bowel or other tubular organ over time.

A need also exists for an annular support structure which operates in conjunction with any end-to-end, annular or circular stapling device to reduce the trauma suffered by the patient, reduce the instances of leakage, reduce the instances of bleeding, and create a relatively strong bond between adjacent body tissues.

SUMMARY

The present disclosure relates to structures and methods for attaching a buttress material to a surgical stapling device for use in anastomosis procedures.

According to one aspect of the present disclosure, a surgical stapling device for joining tissue portions is provided and includes a handle assembly; a tubular body portion supported on a distal end of the handle assembly, the tubular body portion having a staple cartridge assembly containing a plurality of surgical staples within a pair of annular arrays of staple receiving slots formed in a tissue facing surface thereof, the staple cartridge assembly defining a radial inner surface and a radial outer surface; and an anvil assembly at a distal end of the surgical stapling device, the anvil assembly having a shaft for removably connecting the anvil assembly to the tubular body portion, the anvil assembly and tubular body portion being juxtaposed with respect to one another along the shaft and arranged so as to be approximated with respect to one another.

The surgical stapling device further includes a ring-like mounting structure sized to have an outer diameter that frictionally engages the radial inner surface of the staple cartridge assembly, wherein the mounting structure is disposed within the radial inner surface of the staple cartridge assembly; an annular buttress material overlaying the tissue facing surface of the staple cartridge assembly, the annular buttress material defining an outer radial terminal edge extending radially beyond the pair of annular arrays of staple receiving slots, and a radial inner terminal edge extending across the mounting structure; and at least one suture securing the buttress material to the mounting structure.

According to another aspect of the present disclosure, a buttress material and mounting structure assembly is provided for use with a circular surgical stapling device including a staple cartridge assembly containing a plurality of surgical staples within a pair of annular arrays of staple receiving slots formed in a tissue facing surface thereof, the staple cartridge assembly defining a radial inner surface and a radial outer surface. The buttress material and mounting structure assembly includes a ring-like mounting structure sized to have an outer diameter that frictionally engages the radial inner surface of the staple cartridge assembly, wherein the mounting structure is disposed within the radial inner surface of the staple cartridge assembly; an annular buttress material overlaying the tissue facing surface of the staple cartridge assembly, the annular buttress material defining an outer radial terminal edge extending radially beyond the pair of annular arrays of staple receiving slots, and a radial inner terminal edge extending across the mounting structure; and at least one suture securing the buttress material to the mounting structure.

The mounting structure may be fabricated from an elastomeric material.

Each suture may extend through the buttress material and through the mounting structure.

Each suture may include a first end, a second end, and a bridge portion interconnecting the first end and the second end, wherein the first end and the second end of each suture extends through the buttress material and through the mounting structure.

The buttress material may define an annular inner attachment portion; an annular middle staple engaging portion, disposed radially outward of the inner portion; and an annular outer portion, disposed radially outward of the middle portion.

Each suture may extend through the annular inner attachment portion of the buttress material. The first end and the second end of each suture may extend through the buttress material and through the mounting structure.

The bridge portion of each suture may extend in a direction transverse to a central axis of the buttress material.

A proximal and an outer corner of the mounting structure may be chamfered.

According to yet another aspect of the present disclosure, a method is provided of using a buttress material and mounting structure assembly for use with a circular surgical stapling device including a staple cartridge assembly containing a plurality of surgical staples within a pair of annular arrays of staple receiving slots formed in a tissue facing surface thereof, the staple cartridge assembly defining a radial inner surface and a radial outer surface.

The method includes the steps of providing a buttress material and mounting structure assembly including a ring-like mounting structure sized to have an outer diameter that frictionally engages the radial inner surface of the staple cartridge assembly; an annular buttress material overlaying the tissue facing surface of the staple cartridge assembly, the annular buttress material defining an outer radial terminal edge and a radial inner terminal edge; and at least one suture securing the buttress material to the mounting structure.

The method further includes the step of positioning the buttress material and mounting structure assembly at least partially within the cartridge assembly of the surgical stapling device such that the mounting structure is disposed within the radial inner surface of the staple cartridge assembly; and the outer radial terminal edge of the annular buttress material extends radially beyond the pair of annular arrays of staple receiving slots, and the radial inner terminal edge of the annular buttress material extends across the mounting structure.

The method further includes the steps of receiving body tissue between the anvil assembly and the cartridge assembly; grasping the body tissue between the anvil assembly and the cartridge assembly; and firing the surgical stapling device to drive a plurality of staples from the staple cartridge assembly through the buttress material and the body tissue; and sever the buttress material radially outward of the at least one suture.

The mounting structure may be fabricated from an elastomeric material, and the step of positioning the buttress material and mounting structure assembly at least partially within the cartridge assembly of the surgical stapling device may include the elastomeric mounting structure radially engaging the inner surface of the staple cartridge assembly in a press-fit manner.

Any of the above aspects of the present disclosure described may be combined with any other aspect of the present disclosure without departing from the scope of the present disclosure.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein.

DETAILED DESCRIPTION OF EMBODIMENTS

Embodiments of the presently disclosed annular surgical stapling device will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Figure 1:
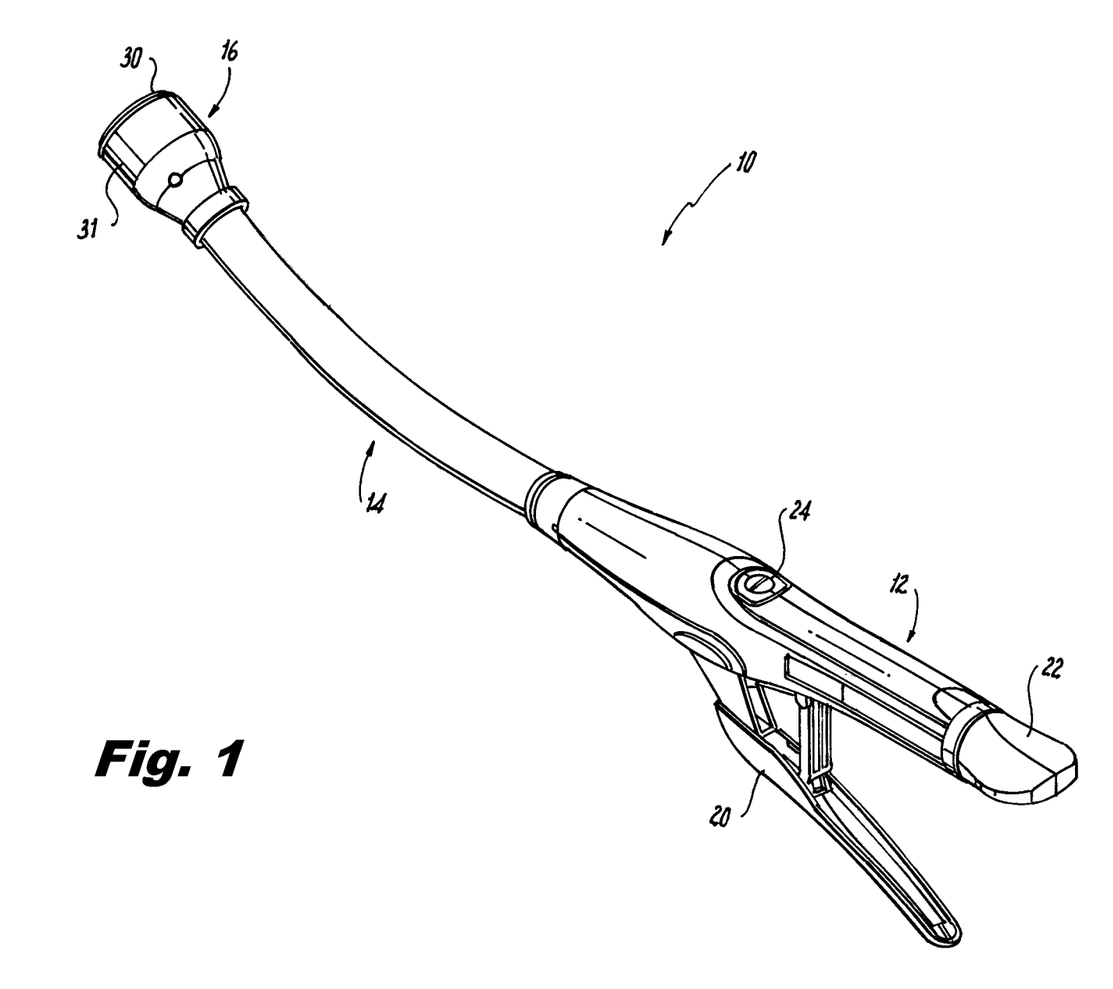
FIG. 1 is a perspective view of an exemplary annular surgical stapling device according to the present disclosure.
Figure 2:
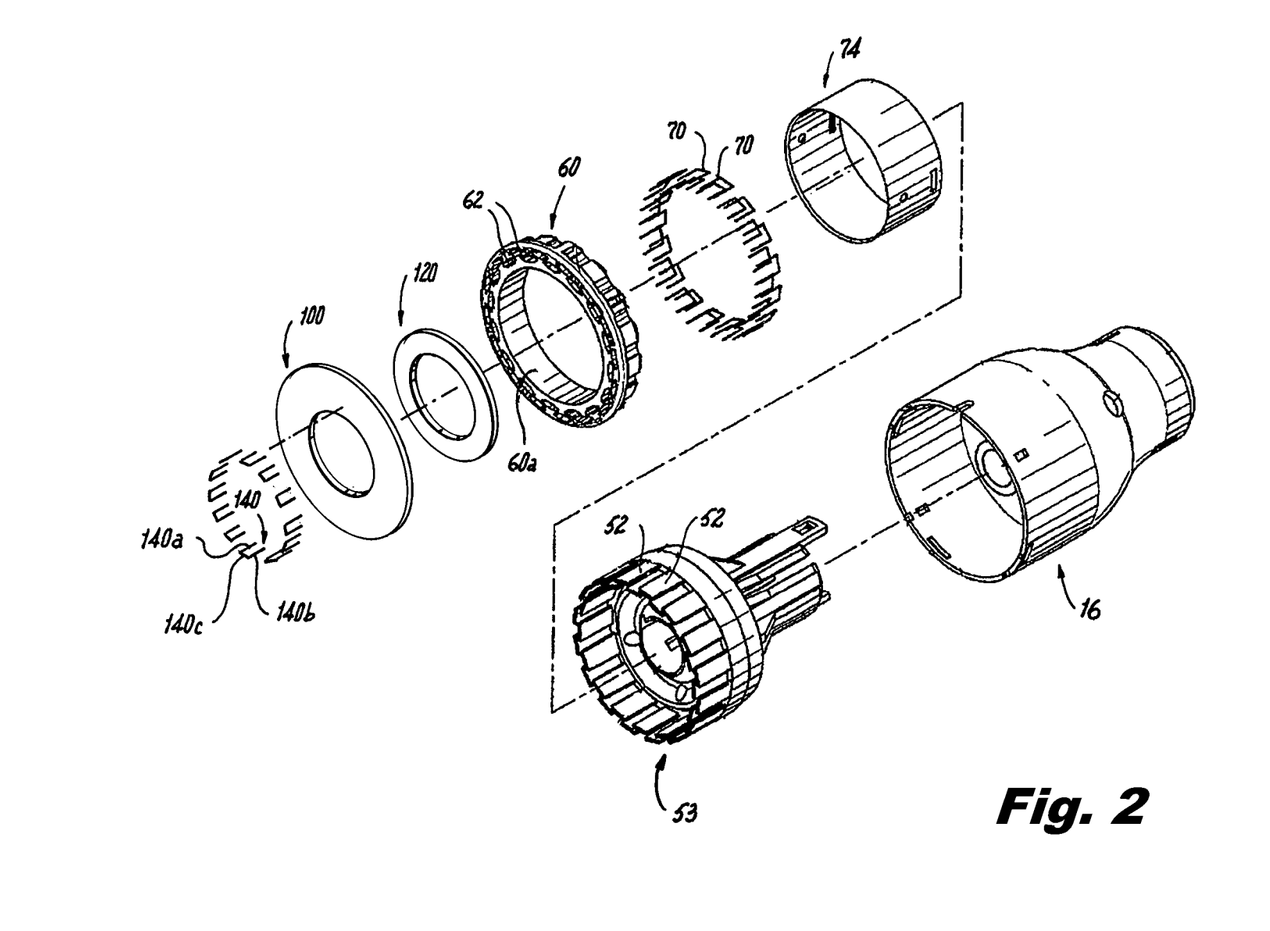
FIG. 2 is a perspective view, with parts separated, of a head portion of the surgical stapling device of FIG. 1.
Figures 3, 4:
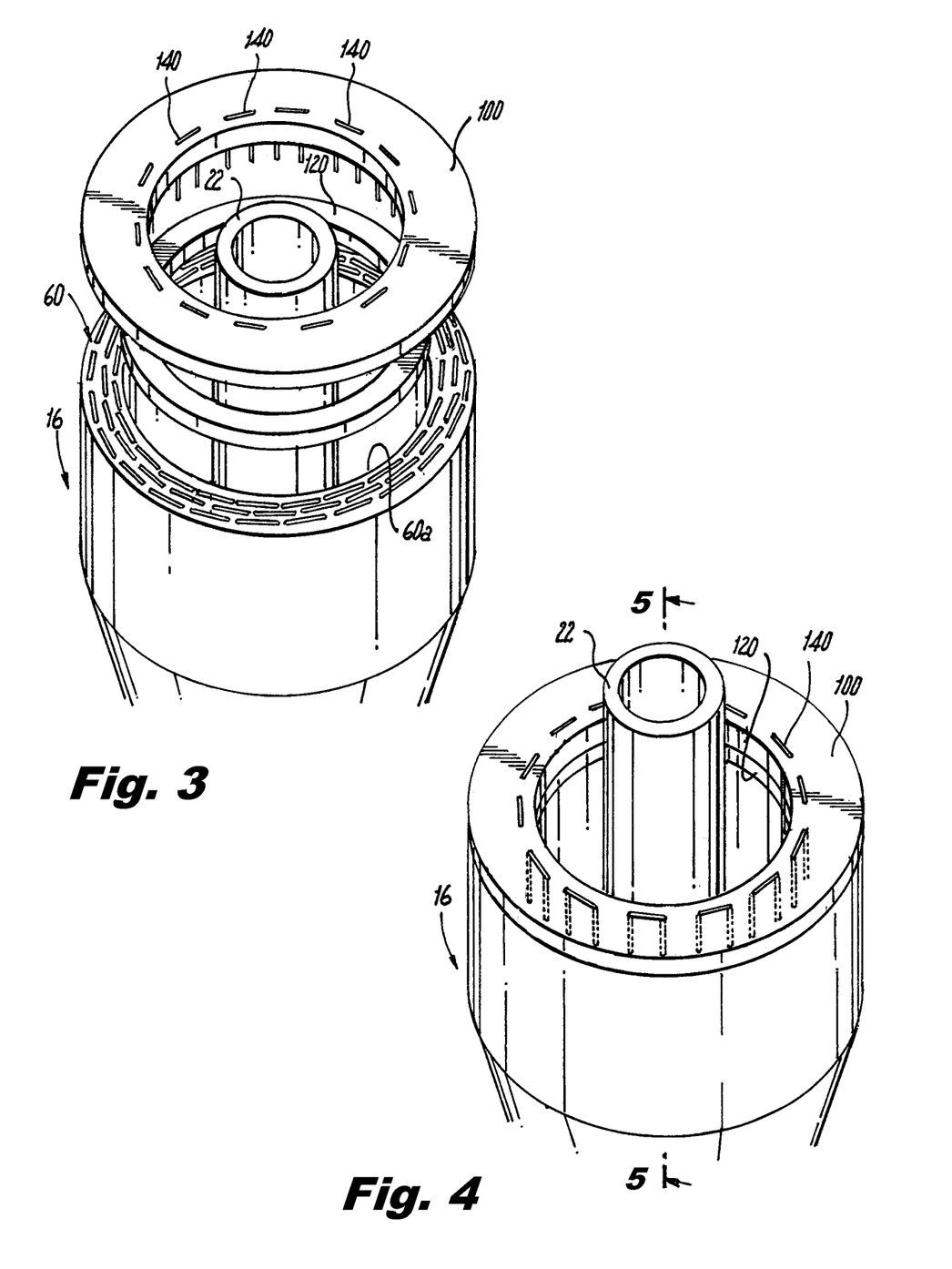
FIG. 3 is a further perspective view of the head portion of the surgical stapling device of FIG. 1, illustrating a buttress material and a mounting structure separated therefrom.
FIG. 4 is another perspective view of the head portion of the surgical stapling device of FIG. 1, illustrating the buttress material connected to the head portion.

Referring initially to FIGS. 1 and 2, an annular surgical stapling device for use with a buttress material is disclosed herein and is generally designated as 10. Surgical stapling device 10 includes a handle assembly 12 having at least one pivotable actuating handle member 20, and an advancing member 22. Extending from handle member 12, there is provided a tubular body or shaft portion 14 which may be constructed so as to have a curved shape along its length. Body or shaft portion 14 terminates in a staple cartridge head assembly 16. Staple cartridge head assembly 16 is configured to receive a staple guide 60 therein. Staple guide 60 includes at least one annular array of staple receiving slots 62 defined in a distal end thereof and a plurality of staples 70 disposed, one each, in each of staple receiving slots 62. For example, staple guide 60 may include one, two, or more than two annular arrays of staple receiving slots 62. Staple receiving slots 62 are defined in a tissue facing or contacting surface of the distal end of the staple guide 60.

Typically, staple cartridge head assembly 16 includes a staple pusher 53 including a proximal portion having a generally frusto-conical shape and a distal portion defining two concentric rings of peripherally spaced fingers 52, each one of which is received within one of the respective staple receiving slots 62 of staple guide 60.

Additionally, staple cartridge head assembly 16 includes a knife 74, substantially in the form of an open cup with the rim thereof defining a knife edge, disposed within staple cartridge head assembly 16 and mounted to staple pusher 53. The knife edge is disposed radially inward of the pair of annular arrays of staples 71 and the pair of annular rows of staple receiving slots 62. Accordingly, in use, as the staple pusher 53 is advanced, the knife 74 is also advanced axially in a linear direction.

Figure 5:
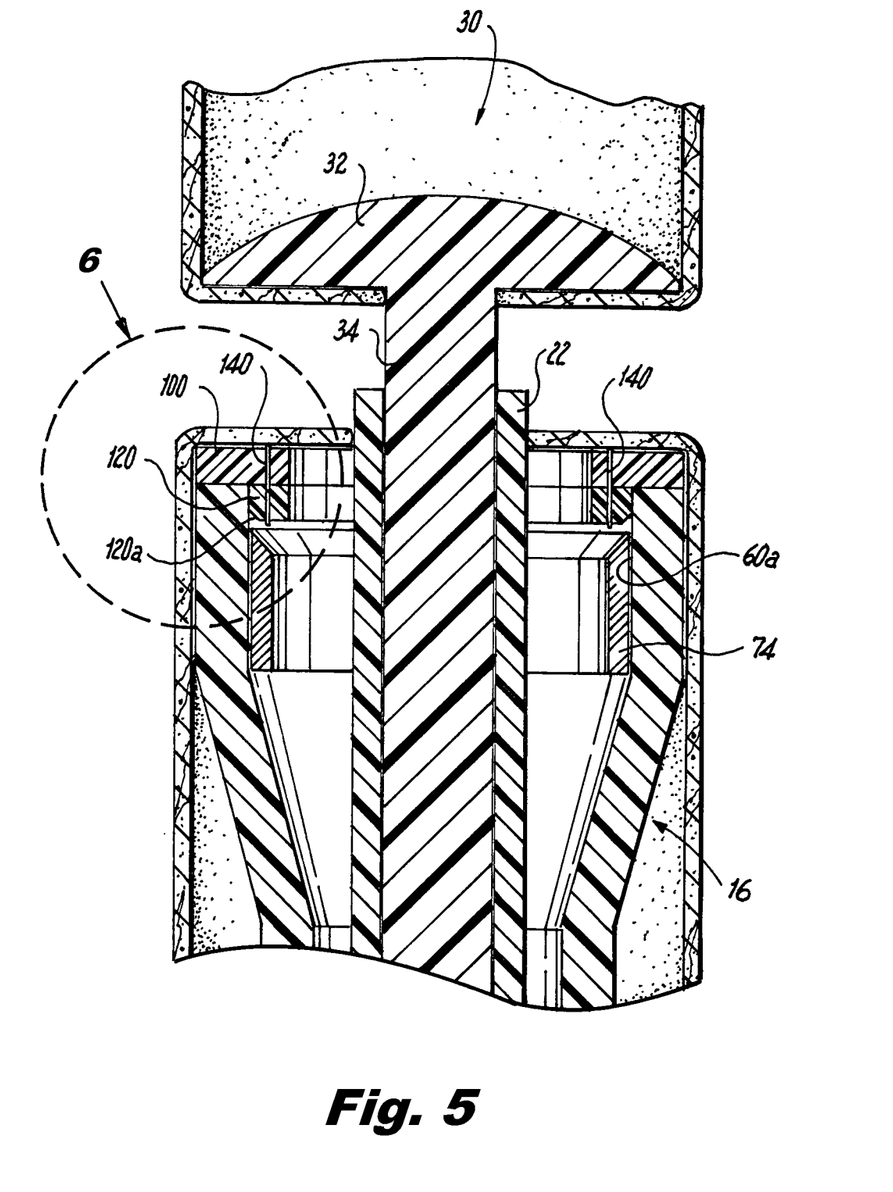
FIG. 5 is cross-sectional view of the head portion and anvil assembly of the surgical stapling device of FIG. 1, as taken through 4-4 of FIG. 5, shown in position between a pair of body lumens.

Positioned distally of staple cartridge head assembly 16 there is provided, as seen in FIGS. 1 and 5, an anvil assembly 30 including an anvil member 32 and a shaft 34 operatively associated therewith for removably connecting anvil assembly 30 to a distal end portion of stapling device 10. Shaft 34 of anvil assembly 30 is connectable to a central shaft 22 of stapling device 10 extending through staple cartridge head assembly 16 and connecting anvil assembly 30 to staple cartridge head assembly 16 of surgical instrument 10.

Reference may be made to U.S. Pat. No. 8,322,590 to Patel et al., the entire contents of which are incorporated herein by reference, for a detailed discussion of the construction and operation of annular stapling device 10.

Referring now to FIGS. 2-6, a buttress material 100 and a mounting structure 120 together form an assembly for connecting buttress material 100 to staple cartridge head assembly 16 is shown and will be described. Buttress material 100 is generally annular in shape and includes an annular inner attachment portion 102; an annular middle staple engaging portion 104, disposed radially outward of inner portion 102; and an annular outer portion 106, disposed radially outward of middle portion 104. A substantially centrally located aperture 108, defined by an inner circumference of inner portion 102 is formed through or within buttress material 100. Buttress material 100 may be any shape sufficient to provide support for anastomosis of tissue after surgical stapling device 10 has been fired including, for example, a rectangle, an oval, a triangle or any other polygonal or other shape.

As illustrated in FIGS. 3-6, buttress material 100 is sized such that when buttress material 100 is positioned over the tissue contacting or facing surface of staple guide 60, outer portion 106 of buttress material 100 is substantially axially aligned with an outer surface of staple cartridge head assembly 16, and annular middle staple engaging portion 104 of buttress material 100 overlies staple retaining slots 62 of staple guide 60. Aperture 108 of buttress material 100 is sized to at least receive shaft 22 of anvil assembly 30 and central shaft 22 of surgical stapling device 10 therethrough. It is also contemplated that buttress material 100 may extend radially beyond an inner surface and the outer surface of staple guide 60.

Buttress material 100 may be fabricated from surgical grade, biocompatible, non-absorbable material (i.e. permanent) or absorbable material (i.e. non-permanent), such as a mesh or other porous or non-porous material desirably optionally containing, impregnated, or coated with an adhesive, sealant and/or other medicament. It is also contemplated that each one or more portions of the buttress may be a composite of include both a non-absorbable and an absorbable material. Suitable materials for the fabrication of buttress material 100 and suitable adhesives, sealants, and/or medicaments for impregnation in or application to buttress material 100 may be found, for example, in U.S. Pat. No. 7,942,890, referenced above.

Buttress material 100 may be secured to staple head assembly 16 through the use of one or more fasteners or sutures 140 stitched to mounting structure 120, as illustrated in FIGS. 2-6. Generally, each suture 140 includes a first end or leg 140a, a second end or leg 140b, and a body or bridge portion 140c extending between and interconnecting the first and second ends 140a, 140b, as will be described in the embodiments to follow.

Similar to buttress material 100, sutures 140 may be fabricated from surgical grade, biocompatible, non-absorbable material (i.e. permanent) or absorbable material (i.e. non-permanent) or material desirably impregnated with an adhesive, sealant and/or other medicament. It is also contemplated that sutures 140 may be a composite of both a non-absorbable and an absorbable material. Suitable materials of sutures 140 are described above with reference to buttress material 100 and may be found, for example, in U.S. Pat. No. 7,942,890, referenced above.

As mentioned above, sutures 140 function to secure buttress material 100 to mounting structure 120. Specifically, each of first and second ends 140a, 140b of sutures 140 may extend through buttress material 100 and extend through mounting structure 120 and may be secured in place to one another through the use of knotting, fusing, heat welding, staking or other similar methods which will limit or prevent first and second ends 140a, 140b of sutures 140 from being withdrawn through or from mounting structure 120. It is contemplated that bridge portion 140c of sutures 140 may rest against a tissue facing or contacting surface of buttress material 100 or against mounting structure 120.

While first and second ends 140a, 140b of sutures 140 are shown and described as extending through mounting structure 120, it is contemplated that first and second ends 140a, 140b of sutures 140 may extend around mounting structure 140 and tie buttress material 100 to mounting structure 120.

Figure 6:
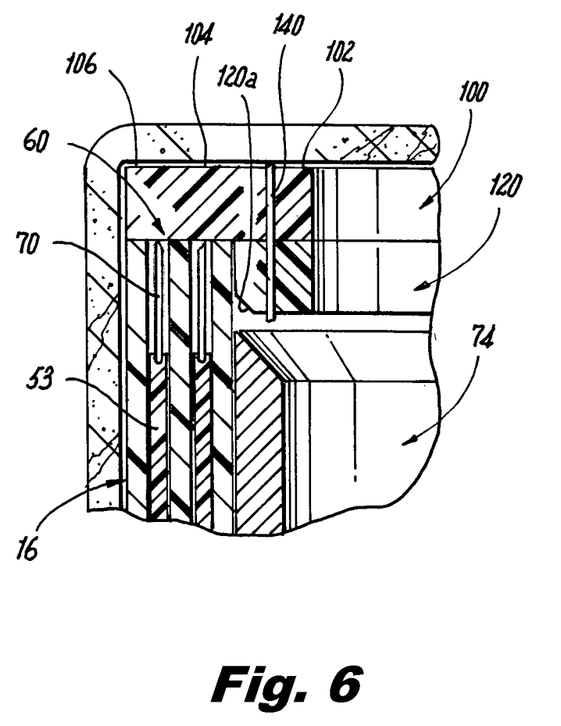
FIG. 6 is an enlarged view of the indicated area of detail of FIG. 5.

As seen in FIGS. 2-6, mounting structure 120 is in the form of a ring that is dimensioned to fit within a circumference of the inner wall 60a of staple guide 60 of staple cartridge head assembly 16, in a press fit manner. In an embodiment, ring 120 is formed from an elastomeric material and has a diameter so as to establish a degree of friction between ring 120 and inner wall 60a of staple guide 60 preventing or inhibiting mounting structure 120 from freely falling out of staple cartridge head assembly 16. It is envisioned that ring 120 may have a substantially circular, transverse, cross-sectional profile, or, as shown in FIGS. 2, 5 and 6, may have a rectangular, transverse, cross-sectional profile. As seen in FIGS. 5 and 6, ring 120 may define a chamfered corner 120a along an outer and proximal edge thereof. In this manner, the knife edge of knife 74 may first enter into the chamfered corner 120a of ring 120 upon firing and thus reduce any tendency of ring 120 to interfere or obstruct the firing of surgical stapling device 10.

Being that ring 120 frictionally engages inner wall 60a of staple guide 60, with buttress material 100 stitched to ring 120 by sutures 140, when ring 120 is situated in staple guide 60, buttress material 100 overlies staple retaining slots 62 of staple guide 60. Specifically, sutures 140 are used to secure annular inner attachment portion 102 of buttress material 100 to ring 120, and annular middle staple engaging portion 104 of buttress material 100 overlies staple retaining slots 62 of staple guide 60.

In use, when surgical stapling device 10 is fired, and staple pusher 53 and knife 74 are advanced, staple pusher 53 expels staples 70 from staple retaining slots 62 of staple guide 60 and into buttress material 100, and knife 74 severs buttress material 100 between annular inner attachment portion 102 and annular middle staple engaging portion 104. By severing buttress material 100 between annular inner attachment portion 102 and annular middle staple engaging portion 104, inner attachment portion 102 may be removed from the surgical site together with surgical stapling device 10, and annular middle staple engaging portion 104 (together with outer portion 106) is secured to the underlying tissue by staples 70.

Figure 7:
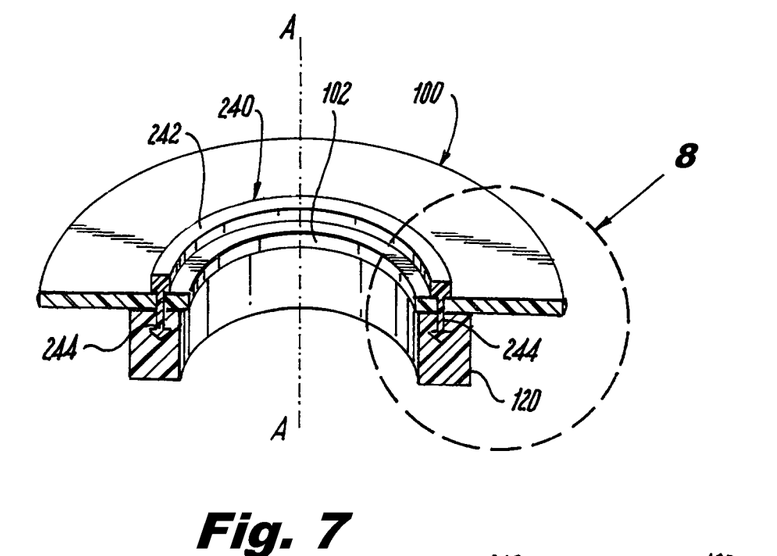
FIG. 7 is a perspective, cross-sectional view, of a fastener according to another embodiment of the present disclosure, for securing the buttress material to the mounting structure.
Figure 8:
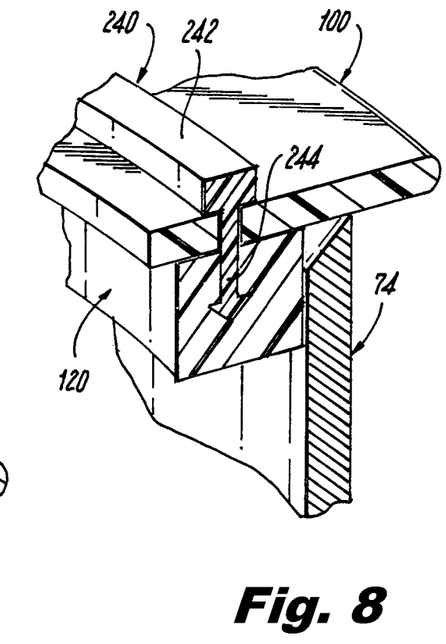
FIG. 8 is an enlarged view of the indicated area of detail of FIG. 7.

Turning now to FIGS. 7 and 8, a fastener for securing buttress material 100 to mounting structure 120, according to another embodiment of the present disclosure, is generally designated as 240. Fastener 240 includes a ring-like body or frame portion 242 having a radial dimension so as to overlie annular inner attachment portion 102 of buttress material 100. Fastener 240 further includes a plurality of barbed pins 244 extending from frame portion 242, in a direction parallel to a central axis "A" of frame portion 242, and in a proximal direction from frame portion 242.

In use, barbed pins 244 penetrate through buttress material 100 and penetrate into or are potted into elastomeric mounting structure 120 to thereby hold buttress material 100 in place relative to mounting structure 120.

Figure 9:
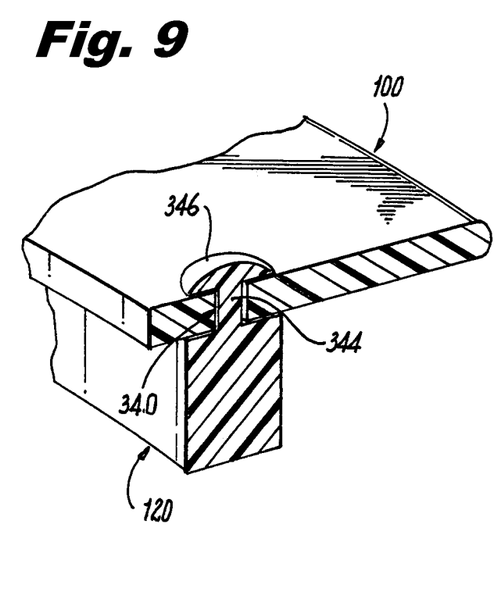
FIG. 9 is an enlarged perspective, cross-sectional view, of a fastener according to another embodiment of the present disclosure, for securing the buttress material to the mounting structure.

Turning now to FIG. 9, a fastener for securing buttress material 100 to mounting structure 120, according to yet another embodiment of the present disclosure, is generally designated as 340. Fastener 340 includes a pin or stem 344 integrally formed with and extending from mounting structure 120. Pins 344 extend from mounting structure 120 in a direction parallel to a central axis of mounting structure 120, and in a distal direction from mounting structure 120. Each pin 344 terminated in a mushroomed head portion 346 that is configured and dimensioned to pass through an aperture, slit or the like formed in buttress material 100, specifically, formed in annular inner attachment portion 102 of buttress material 100.

In use, head portion 346 of fastener 340 extends through buttress material 100 to thereby hold buttress material 100 in place relative to mounting structure 120.

Figure 10:
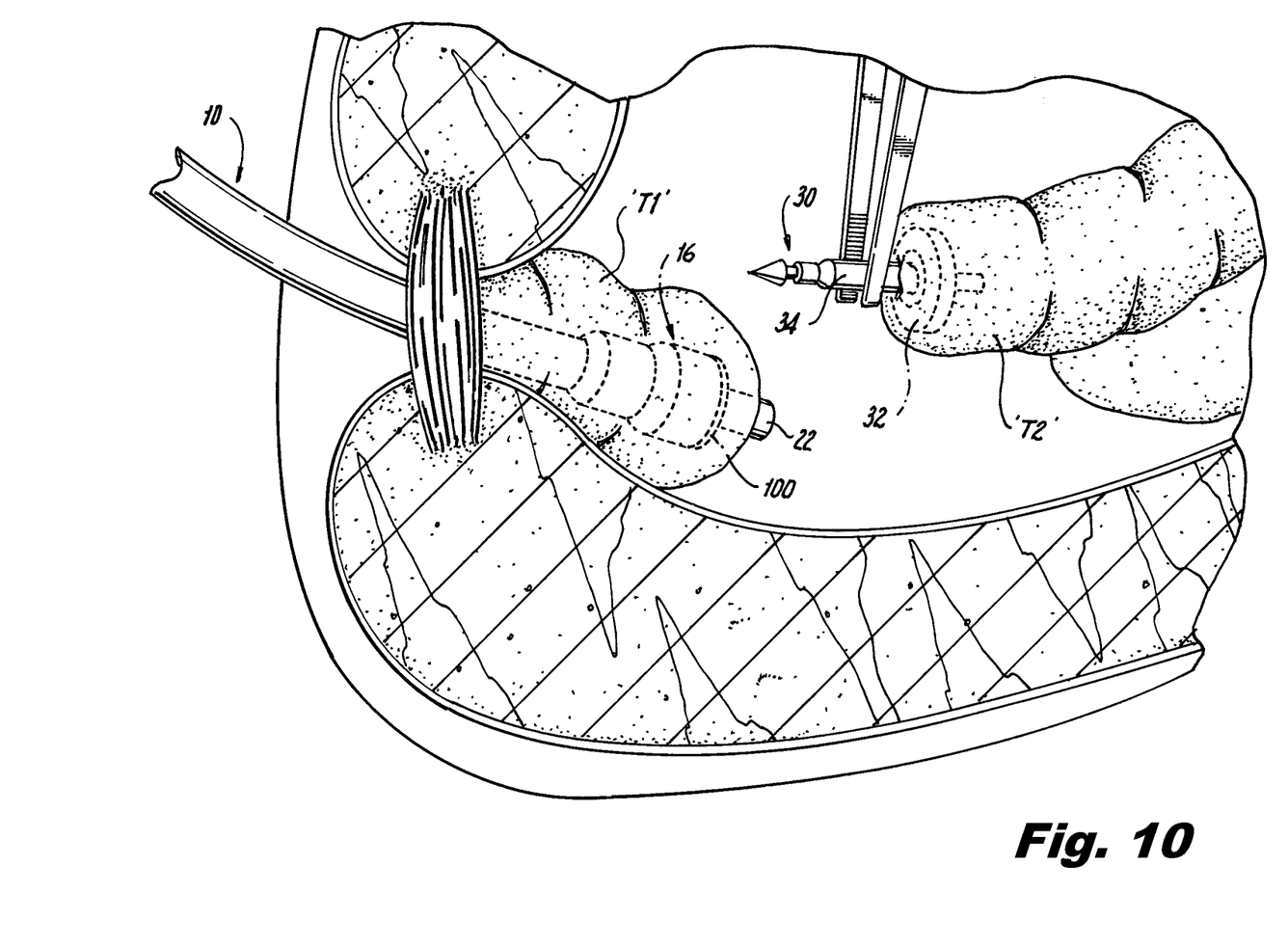
FIG. 10 is a perspective view of the intestinal area of a patient, illustrating a method of positioning the annular surgical stapling device of FIG. 1 to connect the anvil assembly to the tubular body portion.

Turning now to FIG. 10, there is illustrated the use of annular surgical stapling device 10 and detachable anvil assembly 30 in an anastomosis procedure to effect joining of adjacent intestinal sections "T1 and T2". The anastomosis procedure is typically performed using minimally invasive surgical techniques including laparoscopic means and instrumentation. At the point in the procedure shown in FIG. 10, a diseased intestinal section has been previously removed, anvil assembly 30 has been applied to the operative site either through a surgical incision or transanally and positioned within intestinal section "T2", and staple cartridge head assembly 16 of surgical stapling device 10 has been inserted transanally into intestinal section "T1". Intestinal sections "T1 and T2" are also shown temporarily secured about their respective components (e.g., shaft 34 of anvil assembly 30, and the central shaft 22 of staple cartridge head assembly 16 of surgical stapling device 10 by a purse-string suture or the like).

According to one method, with reference to FIG. 10, buttress material 100 may be positioned and secured to the tissue contacting or facing surface of staple guide 60 of staple cartridge head assembly 16 using any of the mounting structures 120 described above. It is envisioned that staple cartridge head assembly 16 and/or surgical stapling device 10 may come with buttress material 100 pre-positioned and secured to the tissue contacting or facing surface of staple guide 60 of staple cartridge head assembly 16. Alternatively the surgeon may secure buttress material 100 to the tissue contacting or facing surface of staple guide 60 of staple cartridge head assembly 16 prior to use.

With buttress material 100 secured in place, the surgeon maneuvers anvil assembly 30 until the proximal end of shaft 34 is inserted into the central shaft 22 of staple cartridge head assembly 16 of surgical stapling device 10. Central shaft 22 is now engaged to shaft 34 with intestinal sections "T1 and T2" disposed between anvil assembly 30 and staple cartridge head assembly 16. As seen in FIGS. 5 and 10, for example, buttress material 100 is disposed between head assembly 16 and intestinal section "T1".

Anvil assembly 30 and staple cartridge head assembly 16 are then approximated to approximate intestinal sections "T1 and T2". Surgical stapling device 10 is then fired to staple buttress material 100 and intestinal sections "T1 and T2" together, and the knife 74 is actuated to cut the portion of tissue and any portion of buttress material 100 (i.e., inner portion 102), to complete the anastomosis. Once anastomosis is complete anvil assembly 30 and staple cartridge head assembly 16 are unapproximated to release intestinal sections "T1 and T2" and buttress material 100 sandwiched therebetween.

In accordance with the present disclosure, it is envisioned that surgical stapling device 10 may be modified for use with a powered actuation assembly. Commonly owned U.S. Pat. No. 8,806,973, the content of which is incorporated by reference herein in its entirety, discloses a surgical device having a powered actuator assembly including powered drive members.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A surgical stapling device for joining tissue portions, comprising:

a cartridge assembly including:
  a staple guide configured to releasably receive a surgical staple; and
  a knife disposed within the cartridge assembly and configured to axially translate therethrough;
an anvil assembly mounted at a distal portion of the cartridge assembly, the anvil assembly configured to move relative to the cartridge assembly between a spaced-apart position and an approximated position; and
a mounting ring disposed within the cartridge assembly such that the mounting ring is coaxially positioned relative to the staple guide, the mounting ring including:
  a distal portion configured to receive at least one first portion of an annular buttress material; and
  a proximal portion having a chamfered edge, wherein the chamfered edge of the mounting ring is positioned to facilitate axial translation of the knife distally beyond the mounting ring.

2. The surgical stapling device according to claim 1, further comprising:
a central shaft extending through the cartridge assembly, wherein the anvil assembly includes an anvil shaft configured to removably connect the anvil assembly to a distal portion of the central shaft extending through the cartridge assembly.

3. The surgical stapling device according to claim 2, wherein the staple guide includes a tissue facing surface configured to receive at least one second portion of the annular buttress material such that the at least one second portion of the annular buttress material extends radially outward beyond the annular array of staple receiving slots and the at least one first portion of the annular buttress material extends radially inward across the distal portion of the mounting ring.

4. The surgical stapling device according to claim 1, wherein the staple guide includes an annular array of staple receiving slots and the knife includes a knife edge disposed radially inward of the annular array of staple receiving slots.

5. The surgical stapling device according to claim 4, wherein the chamfered corner of the mounting ring is disposed radially inward of the knife edge of the knife.

6. The surgical stapling device according to claim 4, wherein the knife edge of the knife is disposed radially between the annular array of staple receiving slots of the staple guide and the chamfered edge of the mounting ring.

7. The surgical stapling device according to claim 4, wherein the chamfered edge of the mounting ring defines a first angle relative to a central axis of the mounting ring and the knife edge of the knife defines a second angle relative to the central axis of the mounting ring, wherein the first angle of the chamfered edge is substantially equal to the second angle of the knife edge.

8. The surgical stapling device according to claim 1, wherein the staple guide includes a radial inner surface and the mounting ring includes an outer diameter configured to frictionally engage the radial inner surface of the staple guide when the mounting ring is coaxially positioned relative to the staple guide.

9. The surgical stapling device according to claim 1, wherein the mounting ring is formed of an elastomeric material.

10. The surgical stapling device according to claim 1, further comprising at least one suture configured to secure the at least one first portion of the annular buttress material to the distal portion of the mounting ring.

11. The surgical stapling device according to claim 10, wherein the at least one suture extends through the at least one first portion of the annular buttress material and the distal portion of the mounting ring.

12. The surgical stapling device according to claim 10, wherein the at least one suture includes a first end portion, a second end portion, and a bridge portion interconnecting the first end portion and the second end portion, wherein the first end portion and the second end portion of the at least one suture extends through the at least one first portion of the annular buttress material and the distal portion of the mounting ring.

13. The surgical stapling device according to claim 10, wherein the at least one suture is configured to extend through an annular attachment portion of the at least one first portion of the annular buttress material.

14. The surgical stapling device according to claim 12, wherein the bridge portion of the at least one suture extends in a direction transverse to a central axis of the mounting ring.

15. The surgical stapling device according to claim 1, wherein the mounting ring is chamfered along an outer corner thereof.

16. The surgical stapling device according to claim 1, further comprising:
a handle assembly; and
a tubular body supported on a distal end portion of the handle assembly, wherein the cartridge assembly is mounted on a distal end portion of the tubular body.

17. A surgical stapling device for joining tissue portions, comprising:
a cartridge assembly including:
  a staple guide configured to releasably receive a surgical staple, the staple guide defining an inner annular wall having a diameter; and
  a knife disposed within the cartridge assembly and configured to axially translate therethrough;
an anvil assembly mounted at a distal portion of the cartridge assembly, the anvil assembly configured to move relative to the cartridge assembly between a spaced-apart position and an approximated position; and
a mounting ring disposed within the cartridge assembly such that the mounting ring is coaxially positioned relative to the staple guide, the mounting ring having a diameter greater than the diameter of the inner annular wall of the staple guide, wherein the mounting ring is frictionally secured within the staple guide.

18. The surgical stapling device according to claim 17, wherein the mounting ring includes:
a distal portion configured to receive at least one first portion of an annular buttress material; and
a proximal portion having a chamfered edge, wherein the chamfered edge of the mounting ring is positioned to facilitate axial translation of the knife distally beyond the mounting ring.

19. The surgical stapling device according to claim 17, wherein the mounting ring is formed of an elastomeric material.

* * * * *